(12) United States Patent
Colledge et al.

(10) Patent No.: US 10,543,196 B2
(45) Date of Patent: *Jan. 28, 2020

(54) ORAL DOSAGE FORMS OF BENDAMUSTINE

(71) Applicant: Astellas Deutschland GmbH, Munich (DE)

(72) Inventors: Jeffrey Colledge, AC Leiderdorp (NL); Margaretha Olthoff, AC Leiderdorp (NL)

(73) Assignee: Astellas Deutschland GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,467

(22) Filed: Jun. 6, 2016

(65) Prior Publication Data

US 2017/0095452 A1   Apr. 6, 2017

Related U.S. Application Data

(63) Continuation of application No. 14/695,527, filed on Apr. 24, 2015, now abandoned, which is a continuation of application No. 13/932,785, filed on Jul. 1, 2013, now abandoned, which is a continuation of application No. 13/132,263, filed as application No. PCT/EP2009/008857 on Dec. 3, 2009, now abandoned.

(30) Foreign Application Priority Data

Dec. 3, 2008 (EP) .................................. 08075915

(51) Int. Cl.
  A61K 31/4184 (2006.01)
  A61K 31/573 (2006.01)
  A61K 45/06 (2006.01)
  A61K 9/00 (2006.01)
  A61K 9/48 (2006.01)

(52) U.S. Cl.
  CPC ........ *A61K 31/4184* (2013.01); *A61K 9/0053* (2013.01); *A61K 9/485* (2013.01); *A61K 9/4825* (2013.01); *A61K 9/4858* (2013.01); *A61K 9/4866* (2013.01); *A61K 9/4875* (2013.01); *A61K 31/573* (2013.01); *A61K 45/06* (2013.01)

(58) Field of Classification Search
  CPC .............. A61K 31/4184; A61K 9/0053; A61K 9/4825; A61K 9/485; A61K 9/4866; A61K 31/573; A61K 45/06
  See application file for complete search history.

(56) References Cited

U.S. PATENT DOCUMENTS

| | | | | |
|---|---|---|---|---|
| 2003/0105141 A1* | 6/2003 | Gao | ..................... | A61K 9/1075 514/341 |
| 2003/0161846 A1* | 8/2003 | Holmberg | ............ | A61K 31/407 424/400 |
| 2006/0128777 A1* | 6/2006 | Bendall | .............. | A61K 31/4184 514/394 |
| 2006/0159713 A1* | 7/2006 | Brittain | ................ | A61K 9/0019 424/400 |
| 2009/0130198 A1* | 5/2009 | Hao | ..................... | A61K 9/1075 424/455 |
| 2009/0324552 A1* | 12/2009 | Lichter | ................ | A61K 9/0046 424/93.4 |

OTHER PUBLICATIONS

Strickley (2004). "Solubilizing Excipients in Oral and Injectable Formulations". Pharmaceutical Research, 21(2): 201-230.*
Toronto Research Chemicals."Bendamustine-d6 (major) Hydrochloride". Retrieved on Apr. 14, 2017. Retrieved from the internet <URL: https://www.trc-canada.com/product-detail/?B132502>.*
Siewert (1995). "FIP Guidelines for Dissolution Testing of Solid Oral Products". Pharm. Ind., 57(5): 362-369.*

* cited by examiner

*Primary Examiner* — Doan T Phan
(74) *Attorney, Agent, or Firm* — Morgan, Lewis & Bockius LLP

(57) ABSTRACT

In the present invention there is provided an oral pharmaceutical composition, comprising bendamustine or a pharmaceutically acceptable, ester, salt or solvate thereof as an active ingredient, and a pharmaceutically acceptable excipient, which is a pharmaceutically acceptable non-ionic surfactant, selected from the group consisting of polyethoxylated castor oil or derivative thereof and a block copolymer of ethylene oxide and propylene oxide.

16 Claims, 2 Drawing Sheets

ORAL DOSAGE FORMS OF BENDAMUSTINE

The present invention relates to oral dosage forms comprising bendamustine or a pharmaceutically acceptable ester, salt or solvate thereof.

BACKGROUND OF THE INVENTION

Bendamustine (4-[5-[bis(2-chloroethyl)amino]-1-methyl-benzimidazo-2-yl]butanoic acid, a nitrogen mustard) is an alkylating agent with bifunctional alkylating activity. It corresponds to the following formula (I):

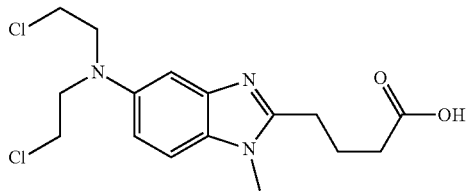

Bendamustine appears to be free of any cross-resistance with other alkylating agents, which offers advantages in terms of chemotherapy for patients who have already received treatment with an alkylating agent.

Bendamustine was initially synthesized in the German Democratic Republic (GDR). The hydrochloric acid of bendamustine was the active ingredient in a commercial product available from 1971 to 1992 under the trade name Cytostasan®. Since that time, it has been marketed in Germany under the trade name Ribomustin® and has been widely used to treat chronic lymphocytic leukemia, non-Hodgkin's lymphoma and multiple myeloma.

The marketed product contains a lyophilized powder of bendamustine hydrochloride which is reconstituted with water for injection yielding a concentrate. This is subsequently diluted with an aqueous solution of 0.9% sodium chloride resulting in the final solution for infusion. This final solution is administered to the patient by intravenous infusion over a period of about 30 to 60 minutes.

Hydrolysis of the bis-2-chloroethylamino-group of bendamustine in water leads to reduction in potency and to impurity formation (B. Maas et al. (1994) in Pharmazie 49: 775-777). Hence administration, usually in a hospital or at least under medical supervision, must occur immediately after reconstitution of the lyophilized powder. Furthermore, reconstitution has been reported to be difficult. It may require more than 30 minutes. Further, it is burdensome and time-consuming for the healthcare professionals responsible for reconstituting the product in the 2 step process.

Preiss et al. (1985) in Pharmazie 40:782-784 compared the pharmacokinetics of bendamustine hydrochloride in plasma in 7 patients after intravenous and oral administration respectively in a dose ranging between 4.2-5.5 mg/kg. The intravenous infusion prepared from the commercially available Cytostasan® product was given over 3 minutes, whereas oral medication in an equivalent dose was taken in the form of capsules, containing 25 mg of bendamustine hydrochloride. The number of capsules to be taken by the patients varied from 10-14, referring to absolute oral doses of 250-350 mg. After oral administration maximal plasma levels were detectable within 1 hour. The mean oral bioavailability was calculated to be 57%, ranging from 25% to 94% indicating a large inter-individual variability (% CV=44%).

Weber (1991) (Pharmazie 46(8): 589-591) investigated the bioavailability of bendamustine hydrochloride in B6D2F1-mice and found that the absorption of the drug from the gastro-intestinal tract is incomplete resulting in a bioavailability of about 40% only.

US 2006/0128777 A1 describes methods for treating cancers, characterised by death-resistant cells and bendamustine-containing compositions in general. Amongst these compositions are oral dosage forms, which are capsules, tablets, pills, powders or granules, wherein the active compound may be admixed with at least one inert excipient, such as sucrose, lactose or starch. However, specific compositions were not exemplified.

Bendamustine hydrochloride is only sparingly soluble in water at a pH of 2.0 and is slightly or very slightly soluble in a range of organic solvents. A good solubility has been observed however in ethanol and methanol. Therefore it is not surprising that the oral bendamustine compositions, as investigated by Preiss et al. and Weber gave rise to relatively poor bioavailability results and a large inter-individual variability.

In view of the stability problems with the intravenous marketed formulation, once reconstituted with water, and in order to improve the patient compliance there has been a long-felt need for a stable dosage-form comprising bendamustine which is easy to administer to the patient and which provides good bioavailability without large inter- and intra-individual variability.

SUMMARY OF THE INVENTION

In order to solve the above problems the present inventors have carried out detailed investigations. They finally succeeded in obtaining the stable pharmaceutical compositions according to the invention. These compositions are suitable for oral administration and comprise bendamustine or a pharmaceutically acceptable ester, salt or solvate thereof as an active ingredient, and at least one pharmaceutically acceptable excipient, which compositions apart from having a good stability also have an improved dissolution profile.

DETAILED DESCRIPTION OF THE INVENTION

Figure 1:
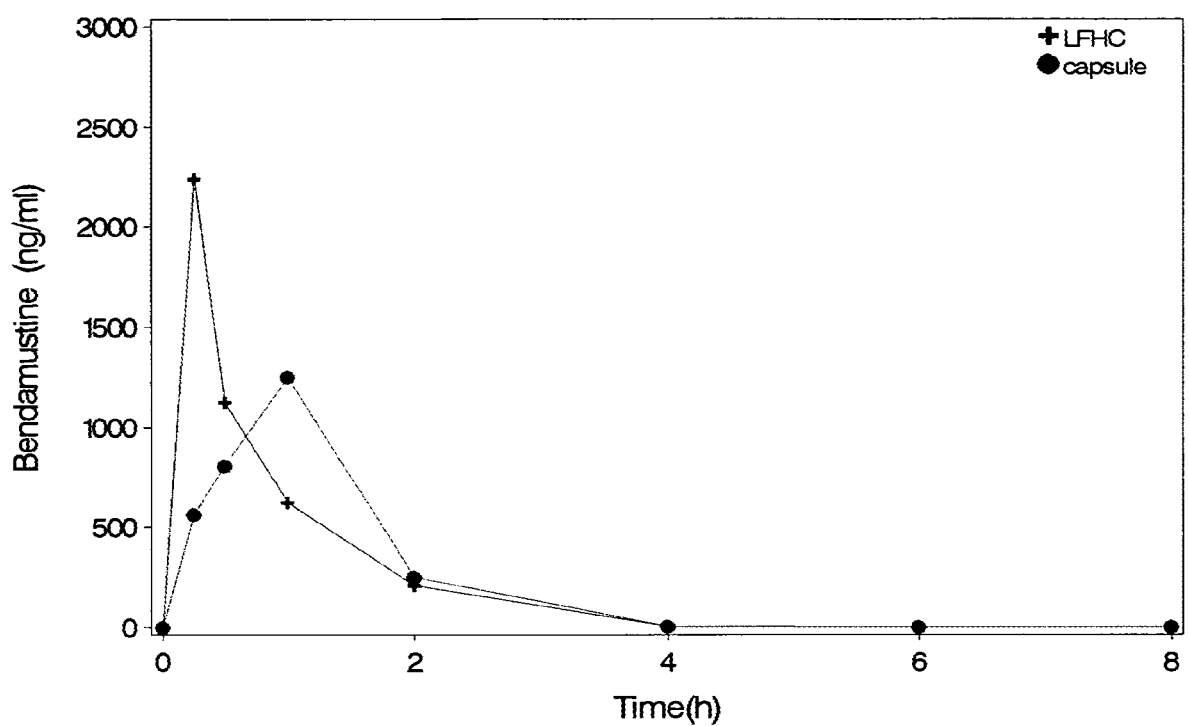
FIG. 1 shows the mean plasma concentration vs. time curve obtained after administering bendamustine hydrochloride in the form of the prior art capsule (reference example 1) and the liquid filled hard capsule formulation of Example 2 to dogs. It is apparent from FIG. 1 that the liquid filled hard capsule formulation provides for a higher maximum concentration of bendamustine, as compared with the prior art reference capsule formulation.

The present invention relates to a pharmaceutical composition for oral administration, the composition comprising bendamustine or a pharmaceutically acceptable, ester, salt or solvate thereof as an active ingredient, and a pharmaceutically acceptable excipient, which is a non-ionic surfactant, selected from the group consisting of a polyethoxylated castor oil or derivative thereof and a block copolymer of ethylene oxide and propylene oxide.

An embodiment is a pharmaceutical composition, comprising bendamustine or a pharmaceutically acceptable ester, salt or solvate thereof and a pharmaceutically acceptable excipient, which is a non-ionic surfactant, selected from the group consisting of a polyethoxylated castor oil or derivative thereof and a block copolymer of ethylene oxide and propylene oxide, wherein the composition is suitable for oral administration by including it into a hard gelatine capsule.

A further embodiment is a pharmaceutical composition for oral administration in a solid dosage-form, which is a hard gelatine capsule, the composition comprising bendamustine or a pharmaceutically acceptable ester, salt or solvate thereof and a pharmaceutically acceptable excipient, selected from the group consisting of a polyethoxylated castor oil or derivative thereof and a block copolymer of ethylene oxide and propylene oxide and preferably selected from the group consisting of macrogol glycerol hydroxystearate, polyoxyl-35-castor oil and ethylene oxide/propylene oxide block copolymer (Pluronic® L44 NF or Poloxamer® 124), wherein the use of the specific non-ionic surfactant leads to a dissolution profile of at least 60% bendamustine dissolved after 20 minutes, 70% dissolved after 40 minutes and 80% dissolved after 60 minutes, as measured with a paddle apparatus at 50 rpm according to the European Pharmacopoeia in 500 ml of a dissolution medium at a pH of 1.5 and preferably it results in a dissolution of at least 60% bendamustine dissolved after 10 minutes, 70% after 20 minutes and 80% after 30 minutes.

A preferred embodiment is a pharmaceutical composition for oral administration in a solid dosage-form, which is a hard gelatine capsule, the composition comprising bendamustine hydrochloride and a pharmaceutically acceptable excipient, which is macrogol glycerol hydroxystearate, wherein the use of the specific non-ionic surfactant results in a dissolution of at least 60% bendamustine dissolved after 10 minutes, 70% after 20 minutes and 80% after 30 minutes, as measured with a paddle apparatus at 50 rpm according to the European Pharmacopoeia in 500 ml of a dissolution medium at a pH of 1.5.

The present invention is based on the surprising finding that stable compositions of bendamustine having a specific and desirable dissolution profile can be obtained by incorporating into the pharmaceutical composition certain non-ionic surfactants. It has been found that if a pharmaceutically acceptable non-ionic surfactant, selected from the group consisting of a polyethoxylated castor oil or derivative thereof and a block copolymer of ethylene oxide and propylene oxide and preferably selected from the group consisting of macrogol glycerol hydroxystearate, polyoxyl-35-castor oil and ethylene oxide/propylene oxide block copolymer (Pluronic® L44 NF or Poloxamer® 124) is used as an excipient in a pharmaceutical composition comprising bendamustine or a pharmaceutically acceptable ester, a salt or a solvate thereof as an active ingredient, a particularly favourable profile of the composition with respect to stability and degradation products, dissolution, bioavailability and a reduced variability in bioavailability is achieved. The incorporation of the above-mentioned non-ionic surfactants in bendamustine-containing compositions results in a dissolution profile of at least 60% bendamustine dissolved after 20 minutes, 70% dissolved after 40 minutes and 80% dissolved after 60 minutes, as measured with a paddle apparatus at 50 rpm according to the European Pharmacopoeia in 500 ml of a dissolution medium at a pH of 1.5 and preferably it results in a dissolution of at least 60% bendamustine dissolved after 10 minutes, 70% after 20 minutes and 80% after 30 minutes.

Below further details of the invention are presented.

The expression "pharmaceutically acceptable ester thereof" describes any pharmaceutically acceptable ester of bendamustine, such as esters with alkyl alcohols and sugar alcohols. Examples of the alkyl alcohols are $C_{1-6}$-alkyl alcohols such as methanol, ethanol, propanol, isopropanol, butanol and tert-butanol. Examples of the sugar alcohols are mannitol, maltitol, sorbitol, erythritol, glycol, glycerol, arabitol, xylitol and lactitol. Preferred examples of the bendamustine esters are the ethyl ester, the isopropyl ester, the mannitol ester and the sorbitol ester, most preferred is the ethylester thereof.

The expression "pharmaceutically acceptable salt thereof" describes any pharmaceutically acceptable salt of bendamustine that administered to a patient (directly or indirectly) provides bendamustine. This term further comprises the pharmaceutically acceptable salt of a bendamustine ester. Nevertheless, it will be considered that the pharmaceutically non-acceptable salts also are included within the limits of this invention since these compounds can be useful in the preparation of pharmaceutically acceptable salts. For example, pharmaceutically acceptable salts of bendamustine are synthesized from the corresponding compound that contains an acid or basic group, by conventional chemical methods. Generally, these salts are, for example, prepared by means of the reaction of free acidic or basic forms of these compounds in a stoichiometric amount with a corresponding base or acid in water or an organic solvent or a mixture of both. Nonaqueous media like ether, ethyl acetate, isopropanol or acetonitrile are generally preferred. Examples of acids which may be used for the salt formation of pharmaceutically acceptable salts of bendamustine include inorganic acids such as hydrochloride, hydrobromide, hydriodide, sulphuric, nitric, and phosphoric acids, and organic acids such as acetic, maleic, fumaric, citric, oxalic, succinic, tartaric, malic, lactic, methylsulphonic and p-toluenesulphonic acids. Pharmaceutically acceptable salts of bendamustine may be derived from either inorganic or organic bases to yield ammonium salts; alkali metal salts (lithium, sodium, potassium, etc.), alkaline earth salts like calcium or magnesium, aluminium salts, lower alkylamine salts like methylamine or ethylamine salts, lower alkyldiamine salts like ethylenediamine salts, ethanolamine, N,N-dialkyleneethanolamine, triethanolamine, and glucamine salts, as well as basic salts of amino acids. Especially preferred are acid salts prepared from the hydrochloride, the hydrobromide, and the hydroiodide, whereas the hydrochloride salt is the most preferred pharmaceutically acceptable salt of bendamustine. The pharmaceutically acceptable salts are produced by conventional techniques well-known in the art.

The expression "pharmaceutically acceptable solvate thereof" describes any pharmaceutically acceptable solvate that, administered to a patient (directly or indirectly) provides bendamustine. This term further comprises the pharmaceutically acceptable solvate of a bendamustine ester. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

It is especially preferred that the active ingredient in the invention's compositions is bendamustine or a pharmaceutically acceptable salt thereof. It is most preferred that the active ingredient is bendamustine hydrochloride.

The dose of the active ingredient in the pharmaceutical composition may readily be determined by the skilled artisan depending on the patient's condition, sex, body weight, body surface area, or age, especially depending on the patient's body weight and body surface area. It is preferred that the daily dosage ranges from about 50 to about 1000 mg, preferably from about 100 to about 500 mg of the active ingredient. The daily dosage may be taken as a single dose or as multiple doses such as twice or three-times daily, most preferably as a single daily dose. The daily dose may be taken once a week or several times a week. The dosage form may contain the amount of a single daily dose or parts thereof. It is preferred that the dosage form of the present invention comprises about 10 to about 1000 mg, preferably about 25 to about 600 mg, more preferably about 50 to about 200 mg and most preferably about 100 mg of the active ingredient.

As used herein, the term "non-ionic surfactant" refers to an amphiphilic compound having a polar, hydrophilic group and a non-polar, lipophilic group or chain and wherein the hydrophilic and lipophylic properties of the compound are characterised by the so-called Hydrophilic-Lipophilic Balance (HLB) value. The non-ionic surfactant to be used for preparing the compositions of the present invention preferably has an HLB-value between 10 and 20 and preferably between 12 and 18. The non-ionic surfactant further has a melting point, pour point or melting range between 5° C. and body temperature (37° C.) and preferably between just below room temperature (20° C.) and body temperature. The material can be in a liquid or a semi-solid state at room temperature. The amphiphilic material is a carrier for the bendamustine active ingredient, which can be present in a dissolved form, a suspended form or partly in a dissolved and partly in a suspended form.

The non-ionic surfactants that are advantageously used for the preparation of the compositions according to the present invention are selected from the group consisting of a polyethoxylated castor oil or derivative thereof and a block copolymer of ethylene oxide/propylene oxide, provided the materials have the afore-mentioned HLB-value and melting point, pour point or melting range.

In one embodiment, the non-ionic surfactant is a polyethoxylated castor oil. One example of a polyethoxylated castor oil is sold under the tradename Cremophor®. Cremophor® products of various purities and viscosities are produced and may be used in the present invention. In particular macrogol glycerol hydroxystearate (Cremophor® RH 40) and polyoxyl-35-castor oil (Cremophor® EL or Cremophor® ELP) can be used. Cremophor® ELP and Cremophor® EL are known as nonionic solubilizers and emulsifiers, produced by reacting castor oil with ethylene oxide in a molar ratio of 1 to 35. They have an HLB-value of 12-14 and a melting point of 26° C. Depending on the ambient temperature these products can be characterised as either semi-solid or as a medium viscosity liquid. Macrogol glycerol hydroxystearate (commercially available as Cremophor® RH 40) is a semi-solid material at 25° C., having a viscosity range at the same temperature of 20-40 cps (as a 30% aqueous solution). It is known as a nonionic solubiliser and emulsifier. It is produced by reacting castor oil with ethylene oxide in a molar ratio of 1 to 45. Its HLB-value ranges from 14-16 and the melting range is from 20-28° C. In experiments it was shown that macrogol glycerol hydroxystearate can advantageously be used on its own for the preparation of compositions according to the present invention.

Pluronic® block copolymers consist of ethylene oxide and propylene oxide blocks. The ethylene oxide units have a hydrophilic character whereas the propylene oxide units have a lipophilic character Variations in the number of hydrophilic ethylene oxide units and lipophilic propylene oxide units results in copolymers with a different molecular mass and different hydrophilic-lipophilic-balance (HLB). Examples of block copolymers of propylene oxide ("PEO")-polypropylene oxide ("PPO") meeting the requirements of the HLB-value and the melting point or pour point or melting range for making the compositions according to the present invention include the commercially available types Pluronic® L35, Pluronic® L 44, Pluronic® L64, Pluronic® P85 and Pluronic® P105. Pluronic® L44 or Poloxamer® 124, but not Pluronic® 68 or Poloxamer® 188 and Pluronic® 127 or Poloxamer® 407. Pluronic® L44 is a preferred non-ionic surfactant.

Except for macrogol glycerol hydroxystearate the above-mentioned non-ionic surfactants are all liquids having a viscosity value which may be too low to avoid sedimentation of the bendamustine hydrochloride. The additional problem to be solved was to find an excipient or a combination of excipients that would allow for a total value for the viscosity of the mixture that would be high enough to avoid segregation of the bendamustine chloride when added to the mixture.

Therefore the compositions according to the present invention, that contain a liquid non-ionic surfactant, advantageously further contain a viscosity improving agent. Suitable viscosity-improving agents include a powder such as colloidal silicon dioxide (commercially available under the trademark Aerosil®) or a semi-solidwaxy material, such as lauroyl macrogol glycerides (commercially available under the trademark Gelucire® 44/14). The amount of the powder or the semi-solid material to be added to the liquid non-ionic surfactant depends on the viscosity of the liquid non-ionic surfactant. Different concentrations have been tested in order to find the minimum suitable amount of viscosity improving agent to be added to visually avoid sedimentation of the active ingredient. Typical relative concentrations of colloidal silicon dioxide to be added range from about 1% to about 8%, but are preferably as low as 1.7% or 2.0% in order not to have a negative impact on the dissolution characteristics of the active ingredient. Typical relative concentrations of lauroyl macrogol glycerides range from 5 to 50%, and are preferably about 10% and about 45%.

Preferred compositions according to the present invention, are disclosed in example 4 and comprise bendamustine hydrochloride in combination with:
  macrogol glycerol hydroxystearate;
  ethylene oxide/propylene oxide block copolymer (Pluronic® L44 NF or Poloxamer® 124), optionally in combination with colloidal silicon dioxide or lauroyl macrogol glycerides (Gelucire® 44/14) and
  polyoxyl-35-castor oil, optionally in combination with lauroyl macrogol glycerides (Gelucire® 44/14).

Further, the compositions of the present invention can include additional excipients, in particular protective agents, such as anti-oxidants and antimicrobial preservatives, e.g. methyl-, ethyl- and propylparaben, as illustrated in examples 1-3. The antioxidant may be d-alpha tocopherol acetate, dl-alpha tocopherol, ascorbyl palmitate, butylated hydroxyanidole, ascorbic acid, butylated hydroxyanisole, butylatedhydroxyquinone, butylhydroxyanisol, hydroxycoumarin, butylated hydroxytoluene, ethyl gallate, propyl gallate, octyl gallate, lauryl gallate, or mixtures thereof. The anti-oxidant is preferably added to compositions containing macrogol glycerol hydroxystearate or polyoxyl-35-castor oil.

The pharmaceutical compositions according to the present invention are advantageously filled into a capsule, which can then easily be taken by the patient.

Two types of capsule are commonly used and are classified according to the nature and flexibility of the capsule shell: soft and hard capsules.

Soft capsules are single unit solid dosage forms comprising a liquid or semi-solid fill. They are formed, filled and sealed in one operation using a rotary die process. They have been used as unit dose containers for liquids for many years, whereas hard capsules have conventionally been used for the delivery of solids in the form of powders, granulates and pellets. Hard capsules are single unit dosage forms, consisting of a cap and a body, which are manufactured separately and which are supplied empty for filling.

Soft capsules are most commonly manufactured from gelatine, to which a plasticiser, usually glycerine or sorbitol, is added in addition to water. Also for hard capsules the most commonly used polymer is gelatine. An additional component is water, which acts as a plasticiser. This component however may be responsible for degradation of active ingredients, such as bendamustine hydrochloride. Therefore as an alternative hard capsules may be manufactured from hydroxypropylmethyl cellulose.

Both soft and hard capsules in addition can include colouring agents and opacifiers.

The preferred type of capsule for the compositions according to the present invention is the hard capsule and more in particular the hard gelatine capsule. Ideally, the materials to be filled into the capsule are fluid at room temperature, which would avoid heating during the filling operation. Generally, heating could result in an easy degradation of the active component.

In principle numerous excipients are available for filling into hard capsules, but in addition to biopharmaceutical considerations, the chemical and physical stability of the final dosage-form are also important to consider, as well as the dissolution profile to produce a safe, effective and stable dosage-form.

Generally, fill formulations for hard capsules may be Newtonian liquids, such as oils, thixotropic or shear thinning gels or semi-solid matrix products that are filled at elevated temperatures and in which the active ingredient is either dissolved or suspended as a fine dispersion. In principle any excipient or mixture of excipients can be used provided that the viscosity of the fill material confirms to the requirements of the filling process. The uniformity of capsule fill weights is important. Further fill formulations should not show stringing and should allow for a clean break from the dosing nozzle.

It has surprisingly been found that the compositions according to the present invention can be advantageously administered in hard gelatine capsules. The particular non-ionic surfactants, selected from the group consisting of a polyethoxylated castor oil or derivative thereof and a block copolymer of ethylene oxide/propylene oxide, and in particular from the group consisting of macrogol glycerol hydroxystearate, polyoxyl-35-castor oil and Pluronic® L44 or Poloxamer® 124, if incorporating bendamustine or a pharmaceutically acceptable ester, salt, or solvate thereof, and after incorporation into hard gelatine capsules result in achieving a good stability, a good dissolution profile and a good bioavailability. To the contrary, if macrogol glycerol hydroxystearate is used in combination with a liquid material, such as bis-diglyceryl polyacyladipate-1 (commercially available as Softisan® 645) and ethylene oxide/propylene oxide block copolymer (commercially available under the names Pluronic® L44 NF or Poloxamer 124), the dissolution profile of bendamustine is deteriorated as compared to compositions containing macrogol glycerol hydroxystearate only. Further it is to be noted that Cremophor® A 25 (ceteareth-25 or macrogol (25) cetostearyl ether) and Cremophor® A 6 (ceteareth-6 and stearylalcohol or macrogol (6) cetostearyl ether) cannot be used as the non-ionic surfactant. Also other commonly used excipients for the preparation of liquid filled capsule preparations were shown to provide no satisfactory results.

The stability of an aqueous solution of bendamustine is strongly influenced by the pH. A significant hydrolytic decomposition of this compound is observed at pH values higher than about 5. At pH>5, the decomposition proceeds rapidly and the resulting content of by-products is high in this pH range. The main hydrolysis products are 4-[5-[(2-Chloroethyl)-(2-hydroxy-ethypamino]-1-methyl-benzimidazo-2-yl]-butanoic acid (HP1), 4-[5-[Bis(2-hydroxyethyl) amino]-1-methyl-benzimidazo-2-yl]-butanoic acid (HP2) and 4-(5-Morpholino-1-methylbenzimidazol-2-yl)-butanoic acid (HP3):

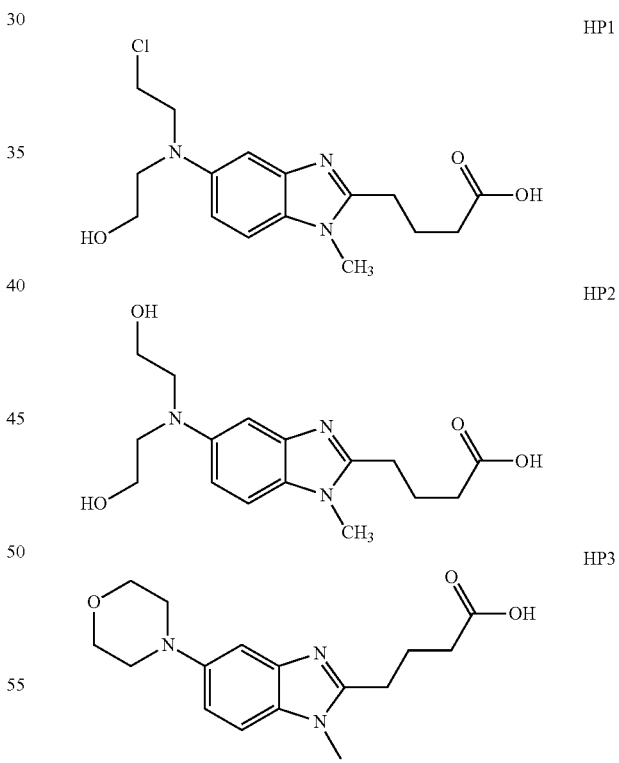

Absorption of an orally administered drug usually happens from the stomach, the small intestine and/or the large intestine. The pH in the stomach is about 1 to 3.5, in the small intestine about 6.5 to 7.6, and in the large intestine about 7.5 to 8.0. Accordingly, for a compound like bendamustine which is prone to degradation in aqueous environments with a pH higher than 5, it is highly preferable that it is absorbed in the stomach, and does not pass through to the small or even the large intestine, in order to avoid decomposition. Hence there is a need for a pharmaceutical composition from which the bendamustine is absorbed completely or at least to a high extent in the stomach, thereby avoiding or reducing the degradation of the bendamustine in the small or large intestine.

It has surprisingly been found that it is possible to solve this problem by using the present pharmaceutical compositions. These compositions comprising bendamustine hydrochloride in a pharmaceutically acceptable excipient, which is a non-ionic surfactant, selected from the group consisting of a polyethoxylated castor oil or derivative thereof and a block copolymer of ethylene oxide and propylene oxide, surprisingly show a fast dissolution, and in particular a dissolution of the bendamustine of at least 60% in 20 minutes, 70% in 40 minutes and 80% in 60 minutes, and preferably of at least 60% in 10 minutes, 70% in 20 minutes and 80% in 30 minutes, as measured with a paddle apparatus at 50 rpm according to the European Pharmacopoeia in an artificial gastric fluid. The artificial gastric fluid as used herein refers to a solution prepared by dissolving 2 g of sodium chloride in 1000 ml of water and then adjusting the pH to 1.5±0.05 with 5 N hydrochloric acid.

Further they have shown to be stable, when put in accelerated stability testing. This is surprising since it has been shown that:
in a reference capsule formulation (see reference example 1) containing bendamustine hydrochloride only in a hard gelatin capsule, when stored at 40° C./75% RH (glass vial open) and 50° C., degradation products were formed within one month of storage. In the case of open vials with 40° C. and 75% RH (relative humidity) the amount of hydrolysis product HP1 was increased by a factor of 4 after one month of storage. For the closed vials the HP1 content is even higher.
in the capsule formulations of reference examples 2, 3 and 4, when stored at 40° C./75% RH (closed glass vial), degradation products were formed within one month of storage and increased upon further storage.

The total time of a drug to pass the stomach to the small intestine is between about 20 minutes to 5 hours, usually between about 30 minutes to 3 hours. Thus pharmaceutical compositions according to this invention advantageously should reduce the degradation of bendamustine in the patient since the bendamustine is released and dissolved to a major extent while in the stomach. Thus even an improved bioavailability of the bendamustine containing compositions according to the invention may be expected.

In a further aspect of this invention the oral pharmaceutical compositions may be used for the treatment or prevention of relapse of a medical condition in a human or animal, preferably a human, which medical condition is selected from chronic lymphocytic leukemia (abbreviated as CLL), acute lymphocytic leukaemia (abbreviated as ALL), chronic myelocytic leukaemia (abbreviated as CML), acute myelocytic leukaemiam (abbreviated as AML), Hodgkin's disease, non-Hodgkin's lymphoma (abbreviated as NHL), multiple myeloma, breast cancer, ovarian cancer, small cell lung cancer, non-small cell lung cancer, and an autoimmune disease.

The present invention also comprises a method of treatment or prevention of relapse of a medical condition selected from chronic lymphocytic leukemia, acute lymphocytic leukaemia, chronic myelocytic leukaemia acute myelocytic leukaemia, Hodgkin's disease, non-Hodgkin's lymphoma, multiple myeloma, breast cancer, ovarian cancer, small cell lung cancer, non-small cell lung cancer, and an autoimmune disease, in a human or animal body comprising administering to the human or animal body in need thereof an effective amount of the pharmaceutical preparation of this invention. Preferably the medical condition is non-Hodgkin's lymphoma.

In another aspect the of this invention the pharmaceutical composition may be administered in combination with at least one further active agent, wherein said further active agent is given prior, concurrently, or subsequently to the administration of the pharmaceutical composition. This at least one further active agent is preferably an antibody specific for CD20 (an examples is rituximab or ofatumumab), an anthracyclin derivative (an example is doxorubicin or daunorubicin), a vinca alkaloid (an example is vincristine), a platin derivative (an example is cisplatin or carboplatin), daporinad (FK866), YM155, thalidomide and analogues thereof (an example is lenalidomide), or a proteasome inhibitor (an example is bortezumib).

The pharmaceutical composition of this invention may also be administered in combination with at least one corticosteroid, wherein said corticosteroid is given prior, concurrently, or subsequently to the administration of the pharmaceutical composition. Examples of the corticosteroids are prednisone, prednisolone and dexamethasone.

The advantage of the compositions according to the present invention further is, that the active ingredient(s), optionally in admixture with one or more excipients, do not need to be provided with a coating in order to further mask the taste of such ingredient and/or to protect the same against possible harmful effects by light and/or moisture such as oxidation, degradation, or to prevent that the subject may experience damage of the oral mucosa, due to the interaction with the active ingredient.

The following examples further illustrate the invention. It will be apparent to the skilled person that these examples are solely for illustrative purposes and must not be considered to limit the invention.

EXAMPLES

1. Capsule Formulations

Reference Example 1: Bendamustine Capsule Formulation (Prior Art)

20.0±1 mg of bendamustine hydrochloride were weighed into the body of an empty hard gelatine capsule, and put into a clear glass HPLC vial (6 ml) of Agilent. Capsules were closed by placing the cap on top of the body and slight pushing.

Capsules were stored at 40° C./75% RH (glass vial open) or 50° C. (glass vial closed). The amount of bendamustine hydrochloride and of related substances was measured with HPLC (column: Zorbax Bonus-RP, 5 μm; temperature of column oven: 30° C.; temperature of autosampler: 5° C.; detector: 254 nm). The results are shown in Table 1:

TABLE 1

Related substances and assay of bendamustine HCl (residual content) in bendamustine capsules

| Storage condition | Related substances | T = 0 | T = 1 month | T = 0 | T = 1 month |
|---|---|---|---|---|---|
| 40° C./75% RH (open vial) | HP1 | 0.10 | 0.45 | 99.64 | 98.83 |
| | NP1*[1] | 0.02 | 0.02 | | |
| | BM1Dimer*[1] | 0.06 | 0.42 | | |
| | BM1EE*[1] | 0.13 | 0.11 | | |

(Bendamustine HCl [% area] columns for T = 0 and T = 1 month)

TABLE 1-continued

Related substances and assay of bendamustine HCl
(residual content) in bendamustine capsules

| Storage condition | Related substances | T = 0 | T = 1 month | T = 0 | T = 1 month |
|---|---|---|---|---|---|
| | HP2 | n.d.*[2] | n.d. | | |
| | HP3 | n.d. | n.d. | | |
| 50° C. (closed vial) | HP1 | 0.10 | 1.46 | 99.64 | 97.51 |
| | NP1 | 0.02 | 0.02 | | |
| | BM1Dimer | 0.06 | 0.24 | | |
| | BM1EE | 0.13 | 0.12 | | |
| | HP2 | n.d. | n.d. | | |
| | HP3 | n.d. | n.d. | | |

*[1]NP1: 4-[6-(2-Chloroethyl)-3,6,7,8-tetra-hydro-3-methyl-imidazo[4,5-h]-[1,4]benzothiazin-2-yl] butanoic acidBM1Dimer: 4-{5-[N-(2-Chloroethyl)-N-(2-{4-[5-bis(2-chloroethyl)amino-1-methylbenzimidazol-2-yl]butanoyloxy}ethyl)amino]-1-methylbenzimidazol-2-yl}butanoic acid
BM1EE: 4-[5-[Bis(2-chloroethyl)amino]-1-methyl-benzimidazo-2-yl] butanoic ethyl ester
*[2]n.d.: not detectable, i.e. beyond detection limit (area percentage less than 0.05%)

Reference Example 2

TABLE 2a

Bendamustine powder mixture for capsules

| Component | mg/dosage-form | Relative Content % |
|---|---|---|
| bendamustine hydrochloride | 55.1 | 21.09 |
| Mannitol | 141.4 | 54.11 |
| Microcrystalline cellulose (Avicel ® PH101) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |

For a batch size of 1000 capsules all excipients except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 259.5 mg (begin)-255.3 mg (end)) and hypromellose capsules (size 2) (mean mass: 255.8 (begin)-253.4 mg (end)) respectively. Capsules were stored at 40° C./75% RH in a closed glass vial. The amount of bendamustine hydrochloride as well as of related substances, like degradation products, by-products of synthesis were measured with HPLC (column: Zorbax Bonus-RP, 5 μm; temperature of column oven: 30° C.; temperature of autosampler: 5° C.; detector: 254 nm). The results are shown in Table 2b (filled in hypromellose capsules) and 2c (filled in gelatine capsules).

TABLE 2b

Bendamustine powder mixture in hypromellose capsules: Related substances and assay of bendamustine HCl (residual content)

| Storage condition | Related substances | T = 0 | T = 2 months | T = 0 | T = 2 months |
|---|---|---|---|---|---|
| 40° C./75% RH (closed vials) | HP1 | 0.18 | 0.87 | 99.49 | 97.92 |
| | HP2 | n.d. | 0.38 | | |
| | HP3 | n.d. | 0.08 | | |
| | NP1 | n.d. | n.d. | | |
| | BM1Dimer | 0.09 | 0.14 | | |
| | BM1EE | 0.16 | 0.14 | | |
| | Unid RRT 0.65*[3] | n.d. | 0.05 | | |
| | Unid RRT 0.68 | n.d. | 0.06 | | |
| | Unid RRT 0.70 | n.d. | 0.19 | | |
| | Unid RRT 0.77 | n.d. | 0.05 | | |
| | Unid RRT 0.93 | n.d. | 0.05 | | |

*[3]Unidentified compound peak at relative retention time of 0.65 as compared to main peak TABLE 2c Bendamustine powder mixture in gelatine capsules: Related substances and assay of bendamustine HCl (residual content)

| Storage condition | Related substances | T = 0 | T = 2 months | T = 0 | T = 2 months |
|---|---|---|---|---|---|
| 40° C./75% RH (closed vials) | HP1 | 0.25 | 1.25 | 99.30 | 97.79 |
| | HP2 | n.d. | 0.11 | | |
| | HP3 | n.d. | <0.05 | | |
| | NP1 | n.d. | n.d. | | |
| | BM1Dimer | 0.14 | 0.14 | | |
| | BM1EE | 0.16 | 0.14 | | |
| | Unid RRT 0.65 | n.d. | 0.05 | | |
| | Unid RRT 0.68 | 0.07 | 0.05 | | |
| | Unid RRT 0.70 | n.d. | 0.30 | | |
| | Unid RRT 0.77 | n.d. | n.d. | | |
| | Unid RRT 0.93 | n.d. | n.d. | | |

Reference Example 3

TABLE 3a

Bendamustine powder mixture for capsules

| Component | mg/dosage-form | Relative Content % |
|---|---|---|
| bendamustine hydrochloride | 55.1 | 21.09 |
| Lactose anhydrous | 141.4 | 54.11 |
| Microcrystalline cellulose (Avicel ®PH112) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |

For 1000 capsules all excipients except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 257.9 mg (begin)-255.2 mg (end)) and hypromellose capsules (size 2) (mean mass: 261.1 (begin)-257.8 mg (end)) respectively.

Capsules were stored at 40° C./75% RH in a closed glass vial. The amount of bendamustine hydrochloride and of related substances was measured with HPLC, as described above. The results are shown in Table 3b (filled in hypromellose capsules) and 3c (filled in gelatine capsules).

TABLE 3b

Bendamustine powder mixture in hypromellose capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.86 | 99.50 | 98.17 |
| | HP2 | n.d. | 0.25 | | |
| | HP3 | n.d. | 0.06 | | |
| | NP1 | n.d. | n.d. | | |
| | BM1Dimer | 0.08 | 0.10 | | |
| | BM1EE | 0.15 | 0.14 | | |
| | Unit RRT 0.68 | n.d. | <0.05 | | |
| | Unit RRT 0.70 | n.d. | 0.19 | | |

TABLE 3c

Bendamustine powder mixture in gelatin capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.23 | 1.35 | 99.38 | 97.74 |
| | HP2 | n.d. | 0.06 | | |
| | HP3 | n.d. | n.d. | | |
| | NP1 | n.d. | n.d. | | |
| | BM1Dimer | 0.13 | 0.10 | | |
| | BM1EE | 0.16 | 0.14 | | |
| | Unit RRT 0.68 | n.d. | 0.05 | | |
| | Unit RRT 0.70 | n.d. | 0.32 | | |

Reference Example 4

TABLE 4a

Bendamustine powder composition for capsules

| Component | mg/dosage-form | Relative Content % |
|---|---|---|
| Bendamustine hydrochloride | 55.1 | 22.04 |
| Lactose anhydrous | 145.15 | 58.06 |
| Microcrystalline cellulose (Avicel ® PH112) | 31.25 | 12.50 |
| Ac-Di-Sol ® | 12.5 | 5.00 |
| Colloidal silicon dioxide (Aerosil ® 200) | 1.0 | 0.40 |
| Magnesium stearate | 2.5 | 1.00 |
| Ascorbic acid | 2.5 | 1.00 |
| Sum | 250 | 100.0 |

For 1000 capsules all excipients except for colloidal silicon dioxide and magnesium stearate were loaded into a Somakon vessel (2.5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter magnesium stearate was added and blending was continued for 1 minute. The blend was subsequently sieved through a 0.5 mm sieve, reloaded into the vessel and blended for another 30 seconds, all at the same conditions.

The blend was transferred to a capsule filling machine (Zanassi AZ 5) and filled into hard gelatine capsules (size 2) (mean mass: 241.3 mg (begin)-244. mg (end)) and hypromellose capsules (size 2) (mean mass: 243.5 (begin)-243. mg (end)) respectively.

Capsules were stored at 40° C./75% RH in a closed glass vial. The amount of bendamustine hydrochloride and of related substances was measured with HPLC, as described above. The results are shown in Table 4b (filled into hypromellose capsules) and 4c (filled in gelatine capsules).

TABLE 4b

Bendamustine powder composition in hypromellose capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.86 | 99.49 | 98.29 |
| | HP2 | n.d. | 0.25 | | |
| | HP3 | n.d. | 0.06 | | |
| | NP1 | n.d. | n.d. | | |
| | BM1Dimer | 0.08 | 0.10 | | |
| | BM1EE | 0.15 | 0.14 | | |
| | Unid RRT 0.57 | n.d. | 0.07 | | |
| | Unid RRT 0.63 | n.d. | 0.05 | | |
| | Unid RRT 0.64 | n.d. | n.d. | | |
| | Unid RRT 0.68 | n.d. | n.d. | | |
| | Unid RRT 0.69 | n.d. | n.d. | | |
| | Unid RRT 0.70 | n.d. | 0.19 | | |
| | Unid RRT 0.75 | n.d. | 0.07 | | |
| | Unid RRT 0.77 | n.d. | 0.05 | | |
| | Unid RRT 0.93 | n.d. | 0.07 | | |

TABLE 4c

Bendamustine powder composition in gelatin capsules: Related substances and assay of bendamustine HCl (residual content)

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.29 | 1.10 | 99.26 | 96.38 |
| | HP2 | n.d. | 0.55 | | |
| | HP3 | n.d. | n.d. | | |
| | NP1 | n.d. | n.d. | | |
| | BM1Dimer | 0.12 | 0.17 | | |
| | BM1EE | 0.15 | 0.15 | | |
| | Unid RRT 0.58 | n.d. | 0.44 | | |
| | Unid RRT 0.62 | n.d. | 0.23 | | |
| | Unid RRT 0.65 | n.d. | 0.10 | | |
| | Unid RRT 0.68 | 0.07 | 0.07 | | |
| | Unid RRT 0.69 | n.d. | 0.06 | | |
| | Unid RRT 0.70 | 0.05 | 0.25 | | |
| | Unid RRT 0.76 | n.d. | 0.17 | | |
| | Unid RRT 0.77 | n.d. | 0.07 | | |
| | Unid RRT 0.77 | n.d. | 0.08 | | |
| | Unid RRT 0.78 | n.d. | 0.09 | | |
| | Unid RRT 0.79 | n.d. | 0.06 | | |
| | Unid RRT 0.91 | n.d. | n.d. | | |
| | Unid RRT 0.94 | n.d. | 0.06 | | |
| | Unid RRT 1.11 | n.d. | n.d. | | |
| | Unid RRT 1.18 | n.d. | n.d. | | |

Example 1

TABLE 5a

Liquid filled hard capsule

| Component | mg/dosage-form | Relative Content % |
|---|---|---|
| bendamustine hydrochloride | 55.1 | 9.18 |
| Pluronic ® L44 NF | 450.70 | 75.12 |
| Cremophor ® RH 40 | 81.85 | 13.64 |
| Softisan ® 645 | — | — |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. Cremophor® RH 40 was melted at 40° C. in a sufficient amount. 5.56 g of the ethanolic solution obtained, 36.83 g of the melted Cremophor® RH 40 and 202.82 g of Pluronic® L44 NF were weighed and mixed at 800 rpm using a mechanical stirrer until the mixture became transparent. The mixture was allowed to solidify by placing it at 10° C. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 25° C. The capsules were closed and sealed. The liquid filled capsules were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC (column: Zorbax Bonus-RP, 5 µm; temperature of column oven: 30° C.; temperature of autosampler: 5° C.; detector: 254 nm). The results are shown in Table 5b.

TABLE 5b

Related substances and assay of bendamustine HCl (residual content)

| Storage condition | Related substances | T = 0 | T = 3 months | T = 0 | T = 3 months |
|---|---|---|---|---|---|
| | | | | Bendamustine HCl [% area] | |
| 40° C./75% RH (closed vial) | HP1 | 0.09 | 0.07 | 98.8 | 98.5 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.08 | | |
| 30° C./65% RH (closed vial) | HP1 | 0.09 | 0.06 | 98.8 | 98.9 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.03 | | |
| 25° C./60% RH (closed vial) | HP1 | 0.09 | 0.07 | 98.8 | 99.0 |
| | NP1 | n.d. | n.d. | | |
| | BM1Dimer | 0.02 | 0.03 | | |
| | BM1EE | 0.15 | 0.15 | | |
| | Individual unknown impurity | 0.01 | 0.03 | | |
| 5° C. (closed vial) | HP1 | 0.09 | 0.07 | 98.8 | 99.8 |
| | NP1 | n.d. | n.d. | | |
| | BM1Dimer | 0.02 | 0.02 | | |
| | BM1EE | 0.15 | 0.15 | | |
| | Individual unknown impurity | 0.01 | n.d. | | |

Example 2

TABLE 6a

Liquid filled hard capsule

| Component | mg/dosage-form | Relative Content % |
|---|---|---|
| bendamustine hydrochloride | 55.1 | 9.18 |
| Pluronic ® L44 NF | — | |
| Cremophore RH 40 | 532.55 | 88.76 |
| Softisan ® 645 | — | |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. Cremophor® RH 40 was melted at 40° C. in a sufficient amount. 5.56 g of the ethanolic solution obtained and 239.65 g of the melted Cremophor® RH 40 were weighed and mixed at 800 rpm using a mechanical stirrer until the mixture became transparent. The mixture was allowed to solidify and cool to room temperature. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 40° C. The capsules were closed and sealed.

The liquid filled capsules so obtained were stored in closed amber glass bottles with screw plugs at 40° C./75%

RH, at 30° C./65% RH, at 25° C./60% RH and at 5° C. The amount of bendamustine hydrochloride as well as of related substances, like degradation products, by-products of synthesis was measured with HPLC, as described above.

The results are shown in Table 6b:

TABLE 6b

Related substances and assay of bendamustine HCl (residual content)

| Storage condition | Related substances*1 | T = 0 | T = 3 months | Bendamustine HCl [% area] T = 0 | T = 3 months |
|---|---|---|---|---|---|
| 40° C./75% RH (closed vial) | HP1 | 0.08 | 0.07 | 100.10 | 99.0 |
| | NP1 | 0.01 | 0.02 | | |
| | BM1Dimer | 0.03 | 0.09 | | |
| | BM1EE | 0.16 | 0.17 | | |
| | Individual unknown impurity | 0.02 | 0.09 | | |
| 30° C./65% RH (closed vial) | HP1 | 0.08 | 0.06 | 100.1 | 100.4 |
| | NP1 | 0.01 | n.d. | | |
| | BM1Dimer | 0.03 | 0.04 | | |
| | BM1EE | 0.16 | 0.13 | | |
| | Individual unknown impurity | 0.02 | 0.03 | | |
| 25° C./60% RH (closed vial) | HP1 | 0.08 | 0.10 | 100.1 | 100.3 |
| | NP1 | 0.01 | n.d. | | |
| | BM1Dimer | 0.03 | 0.03 | | |
| | BM1EE | 0.16 | 0.14 | | |
| | Individual unknown impurity | 0.02 | 0.02 | | |
| 5° C. (closed vial) | HP1 | 0.08 | 0.09 | 100.1 | 99.5 |
| | NP1 | 0.01 | 0.01 | | |
| | BM1Dimer | 0.03 | 0.03 | | |
| | BM1EE | 0.16 | 0.15 | | |
| | Individual unknown impurity | 0.02 | 0.02 | | |

Example 3

TABLE 7a

Liquid filled hard capsule

| Component | mg/dosage-form | Relative Content % |
|---|---|---|
| Bendamustine hydrochloride | 55.1 | 9.18 |
| Pluronic ® L44 NF | — | — |
| Cremophor ® RH 40 | 81.85 | 13.64 |
| Softisan ® 645 | 450.70 | 75.12 |
| Methyl paraben | 1.20 | 0.20 |
| Propyl paraben | 0.12 | 0.02 |
| Butyl hydroxytoluene | 0.12 | 0.02 |
| Ethanol | 10.91 | 1.82 |

0.68 g of methylparaben, 0.068 g of propylparaben and 0.068 g of butylhydroxytoluene were weighed and dissolved in 6.14 g of ethanol. Cremophor® RH 40 was melted at 40° C. in a sufficient amount. 5.56 g of the ethanolic solution obtained, 36.83 g of the melted Cremophor® RH 40 and 202.82 g of Softisan® 645 were weighed and mixed at 800 rpm using a mechanical stirrer until the mixture became transparent. The mixture was allowed to solidify by placing it at 10° C. 24.80 g of bendamustine hydrochloride was subsequently added to the solidified blend by manual stirring and then distributed over the blend by homogenisation using an Ultraturrax T18 high speed homogeniser at 15500 rpm for 10 minutes. The homogenised suspension was filled into hard gelatine capsules with a CFS 1200 capsule filling and sealing machine, operated at 30° C. The capsules were closed and sealed. The liquid filled capsules were stored in closed amber glass bottles with screw plugs at 40° C./75% RH, at 30° C./65% RH, at 25° C./60% RH and at 5° C. The amount of bendamustine hydrochloride as well as of related substances, like degradation products, by-products of synthesis was measured with HPLC, as described above. The results are shown in Table 7b:

TABLE 7b

Related substances and assay of bendamustine HCl (residual content)

| Storage condition | Related substances*1 | T = 0*2 | T = 3 months | Bendamustine HCl [% area] T = 0 | T = 3 months |
|---|---|---|---|---|---|
| 40° C./75% RH (closed vial) | HP1 | 0.08 | 0.06 | 99.6 | 99.5 |
| | NP1 | n.d. | 0.01 | | |
| | BM1Dimer | 0.03 | 0.36 | | |
| | BM1EE | 0.15 | 0.26 | | |
| | Individual unknown impurity | 0.03 | 0.13 | | |
| 30° C./65% RH (closed vial) | HP1 | 0.08 | 0.11 | 99.6 | 99.9 |
| | NP1 | n.d. | n.d. | | |
| | BM1Dimer | 0.03 | 0.09 | | |
| | BM1EE | 0.15 | 0.17 | | |
| | Individual unknown impurity | 0.03 | 0.04 | | |
| 25° C./60% RH (closed vial) | HP1 | 0.08 | 0.11 | 99.6 | 100.0 |
| | NP1 | n.d. | n.d. | | |
| | BM1Dimer | 0.03 | 0.09 | | |
| | BM1EE | 0.15 | 0.17 | | |
| | Individual unknown impurity | 0.03 | 0.04 | | |
| 5° C. (closed vial) | HP1 | 0.08 | 0.07 | 99.60 | 100.1 |
| | NP1 | n.d. | 0.01 | | |
| | BM1Dimer | 0.03 | 0.03 | | |
| | BM1EE | 0.15 | 0.15 | | |
| | Individual unknown impurity | 0.03 | 0.02 | | |

Example 4

TABLE 8 further Liquid filled hard capsule formulations

| | Relative content (%) | | | | | | |
|---|---|---|---|---|---|---|---|
| Component | Ex 4.1 | Ex 4.2 | Ex 4.3 | Ex 4.4 | Ex 4.5 | Ex 4.6 | Ex 4.7 |
| Pluronic ® L44 | — | 88.2 | — | 45.4 | — | 90.8 | — |
| Cremophor ® EL | — | — | 80.7 | — | 90.8 | — | 88.4 |
| Cremophor ® RH 40 | 90.8 | — | — | — | — | — | — |
| Gelucire ® 44/14 | — | — | 10.0 | 45.4 | — | — | — |
| Colloidal silicon dioxide | — | 2.0 | — | — | — | — | 1.7 |
| Bendamustine HCl | 9.2 | 9.8 | 9.3 | 9.2 | 9.2 | 9.2 | 9.9 |

2. Disintegration and Dissolution Tests

Example 5

Disintegration tests for the liquid filled capsule formulations of examples 1, 2 and 3 were carried out in 1000.0 ml of buffer solution pH=1.0±0.05, using disintegration Apparatus A, operated at 37.0° C.±0.5° C. The results are listed in Tables 8a, 8b and 8c.

Example 6

Dissolution tests for the liquid filled capsule formulations of examples 1, 2 and 3 were carried out in artificial gastric acid solution at pH 1.5 (see Ph Eur: 2.9.3: Dissolution test for solid dosage forms in Recommended Dissolution Media).

The dissolution samples were tested for assay by HPLC (column: Zorbax Bonus-RP, 5 μm; temperature of column oven: 30° C.; temperature of autosampler: 5° C.; detector: 254 nm). Artificial gastric fluid pH 1.5 was prepared by placing 250.0 mL of 0.2M potassium chloride 0.2M into a 1000 mL volumetric flask, adding 207.0 mL of 0.2 M hydrochloric acid, then diluting to 1000 mL with Milli-Q water. The pH was measured and adjusted, if necessary, with 2N hydrochloric acid or 2N potassium hydroxide to a pH of 1.5±0.05.

The dissolution test was conducted according to Chapter 2.9.3. of European Pharmacopoeia 6.0, using Apparatus 2 (Paddle-apparatus). The rotation speed of the paddle was 50 rpm, the temperature was 37° C.±0.5° C., the amount of dissolution medium was 500 ml.

The results for the liquid filled hard capsules of examples 1, 2 and 3 are shown in Tables 9a, 9b and 9c:

TABLE 9a

Liquid filled hard capsules of example 1

| Test | T = 0 months | T = 3 months |
|---|---|---|
| *Temperature 40° C. 75% RH* | | |
| Disintegration (minute:second) | 03:23 | 03:30 |
| Dissolution (%) pH 1.5 | Not tested | |
| 10' | | 10.4 |
| 20' | | 35.1 |
| 30' | | 51.1 |
| *Temperature 30° C. 65% RH* | | |
| Disintegration (minute:second) | 03:23 | 03:26 |
| Dissolution (%) pH 1.5 | Not tested | |
| 10' | | 7.0 |
| 20' | | 24.0 |
| 30' | | 54.6 |
| *Temperature 25° C. 60% RH* | | |
| Disintegration (minute:second) | 03:23 | 03:33 |
| Dissolution (%) pH 1.5 | Not tested | |
| 10' | | 37.4 |
| 20' | | 52.4 |
| 30' | | 71.6 |
| *Temperature 5° C.* | | |
| Disintegration (minute:second) | 03:23 | 03:23 |
| Dissolution (%) pH 1.5 | Not tested | |
| 10' | | 57.0 |
| 20' | | 76.7 |
| 30' | | 83.1 |

TABLE 9b

Liquid filled hard capsule of example 2

| Test | T = 0 months | T = 3 months |
|---|---|---|
| *Temperature 40° C. 75% RH* | | |
| Disintegration (minute:second) | 03:52 | 02:58 |
| Dissolution (%) pH 1.5 | Not tested | |
| 10' | | 65.2 |
| 20' | | 88.7 |
| 30' | | 102.0 |
| *Temperature 30° C. 65% RH* | | |
| Disintegration (minute:second) | 03:52 | 03:09 |
| Dissolution (%) pH 1.5 | Not tested | |
| 10' | | 48.1 |
| 20' | | 80.9 |
| 30' | | 93.7 |
| *Temperature 25° C. 60% RH* | | |
| Disintegration (minute:second) | 03:52 | 02:53 |
| Dissolution (%) pH 1.5 | Not tested | |
| 10' | | 54.5 |
| 20' | | 80.7 |
| 30' | | 94.4 |
| *Temperature 5° C.* | | |
| Disintegration (minute:second) | 03:52 | 02:56 |
| Dissolution (%) pH 1.5 | Not tested | |
| 10' | | 57.9 |
| 20' | | 90.0 |
| 30' | | 98.0 |

TABLE 9c

Liquid filled hard capsule of example 3

| Test | T = months | T = 3 months |
|---|---|---|
| *Temperature 40° C. 75% RH* | | |
| Disintegration (minute:second) | 03:59 | 03:36 |
| Dissolution (%) pH 1.5 | Not tested | |
| 10' | | 28.5 |
| 20' | | 49.1 |
| 30' | | 62.9 |
| *Temperature 30° C. 65% RH* | | |
| Disintegration (minute:second) | 03:59 | 03:34 |
| Dissolution (%) pH 1.5 | Not tested | |
| 10' | | 17.5 |
| 20' | | 35.2 |
| 30' | | 58.1 |
| *Temperature 25° C. 60% RH* | | |
| Disintegration (minute:second) | 03:59 | 03:27 |
| Dissolution (%) pH 1.5 | Not tested | |
| 10' | | 25.9 |
| 20' | | 44.2 |
| 30' | | 62.1 |
| *Temperature 5° C.* | | |
| Disintegration (minute:second) | 03:59 | 03:18 |
| Dissolution (%) pH 1.5 | Not tested | |
| 10' | | 15.9 |
| 20' | | 31.1 |
| 30' | | 46.6 |

As may be taken from the above Tables 9a, 9b and 9c, only the liquid filled hard capsule formulation of example 2 according to the invention shows the preferred fast dissolution profile of bendamustine, which is at least 60% in 10 minutes, 70% in 20 minutes and 80% in 30 minutes, as measured with a paddle apparatus at 50 rpm according to the European Pharmacopoeia in 500 ml of an artificial gastric fluid.

Example 7

TABLE 10 results of analytical tests on formulations of example 4

| Analytical Test | Limits | Ex. 4.2 | Ex. 4.7 | Ex 4.3 | Ex 4.5 | Ex 4.6 | Ex. 4.4 | Ex 4.1 |
|---|---|---|---|---|---|---|---|---|
| Identification (HPLC) | Positive | Positive | Positive | Positive | Positive | Positive | Positive | Positive |
| Content uniformity | Complies | N/A | N/A | N/A | Complies | Complies | Complies (RSD 4.40) | Complies (RSD 2.66) |
| Assay (HPLC) | 95.0%-105.0% | 98.2 | 101.0 | 117.9 | 98.6 | 103.3 | 95.8 | 98.0 |
| Related substances (HPLC) | | | | | | | | |
| HP1 | =0.50% | 0.30 | 0.30 | 0.11 | 0.13 | 0.07 | 0.07 | 0.05 |
| BM1 Dimer | =0.20% | 0.05 | 0.04 | 0.04 | 0.05 | 0.04 | 0.04 | 0.04 |
| BM1EE | =0.50% | 0.14 | 0.15 | 0.15 | 0.14 | 0.15 | 0.14 | 0.14 |
| NP1 | =0.20% | 0.01 | 0.01 | 0.01 | 0.01 | 0.01 | 0.01 | 0.01 |
| Ind. Unknown impurity | =0.10% | 0.04 | 0.14 | 0.04 | 0.05 | 0.02 | 0.01 | 0.03 |
| Total impurities | =1.50% | 0.54 | 0.68* | 0.35 | 0.38 | 0.29 | 0.27 | 0.29 |
| Total impurities after 3 months' storage at 40°/75% RH | | 0.35 | 1.12 | | | | | 1.12 |
| Dissolution Test (Medium: buffer pH = 1.5) | | | | | | | | |
| (% 10 min) | 80% in 30 min | 96.9 | 25.6 | 67.3 | 46.8 | 95.7 | 65.3 | 56.9 |
| (% 20 min) | | 97.1 | 46.5 | 96.2 | 74.3 | 96.7 | 102.5 | 80.4 |
| (% 30 min) | | 96.7 | 72.4 | 104.5 | 88.9 | 95.0 | 109.5 | 93.8 |
| Dissolution test after 3 months' storage at 40°/75% RH; (% 30 min) | | 91 | 72 | | | | | 92 |

3. In Vivo Tests

Example 8

The liquid filled hard capsules of example 2, containing 50 mg of bendamustine, were orally administered to male and female beagle dogs in comparison with the capsules of reference example 1 in order to determine the bioavailability of 1 dose (i.e. 50 mg) of bendamustine (AUC and Cmax) and to determine the level of variability in bioavailability of these capsule formulations: (i.e. % CV on AUC and Cmax). A further formulation (formulation X) was also included in the test but since this formulation was outside the scope of the present invention no details are provided. The total number of animals required was 16.

The basic study design was a cross-over design with 8 animals per arm.

Period 1 (Single Dose of Capsule, Day 1):

| Group | Treatment | Composition | Dose # (mg) | Number of animals |
|---|---|---|---|---|
| 1 | Bendamustine | Reference Capsule | 50 | 4 Male + 4 Female |
| 2 | Bendamustine | Reference Capsule | 50 | 4 Male + 4 Female |

There was a one week wash-out period.

Period 2 (1 Week after Period 1, Single Dose of Either of the Following Formulations, Day 8):

| Group | Treatment | Composition | Dose # (mg) | Number of animals |
|---|---|---|---|---|
| 1 | Bendamustine | Formulation example 2 | 50 | 4 Male + 4 Female |
| 2 | Bendamustine | Formulation X | 50 | 4 Male + 4 Female |

The mean plasma profiles vs. time for both the capsule formulation (reference example 1) and the liquid filled capsule formulation of Example 2 are shown in FIG. 1.

Example 9

An open label, randomized two-way crossover study to assess the absolute bioavailability of oral bendamustine in patients with cancer was conducted to assess the absolute bioavailability of bendamustine administered as an oral formulation (example 2). Besides assessing the pharmacokinetics of bendamustine in plasma following oral and i.v. administration, a further objective was to evaluate the safety and tolerability of bendamustine following i.v. and especially oral administration of the formulation of example 2.

6 Patients resided in hospital for 2 periods; Day −1 to 2 (period 1) and Day 7-9 (period 2). Patients were enrolled to receive in a random order one of the following two treatments on Day 1 and 8:

a single oral dose of 110.2 mg (2×55.1 mg) bendamustine hydrochloride (HCl), being equivalent to about 100 mg bendamustine free base and a single i.v. dose of 100 mg bendamustine HCl, equivalent to 90.7 mg bendamustine free base.

The dose of bendamustine HCl (100 mg intravenous, 110.2 mg orally) was selected based on the safety of the oral formulation in preclinical studies and based on the safety of the registered i.v. formulation.

Blood samples were taken on days 1 and 2 and 8 and 9 to determine the pharmacokinetics of bendamustine and its metabolites in plasma after oral and i.v. administration of bendamustine. The time-points were chosen based on data from the literature (Preiss 1985) following i.v. administration of bendamustine. Preiss and co-workers reported a mean bioavailability of bendamustine of 57% (range: 25-94%; % CV=44%) after oral administration of bendamustine as capsule at doses of 250-350 mg in patients with cancer.

Bendamustine was administered on days 1 and 8 in the morning either orally or intravenously as a single dose (as bendamustine hydrochloride 100 mg i.v. or 110.2 mg orally).

Bendamustine was administered orally as two liquid-filled hard-shell capsules with 250 mL of water or as i.v. infusion over 30 minutes.

Patients had to fast overnight for at least 8 hours before oral and i.v. administration of bendamustine in the morning, except for drinking water which is allowed up to 2 hours prior to administration of study medication. Patients are allowed to have a light breakfast 2 hours after each administration.

The total duration of the admission period was 6 days (day −1 to 2 and day 7-9) excluding screening and a post study visit.

Certain medication was prohibited from 2 weeks before the first administration of the first study drug.

Figure 2:
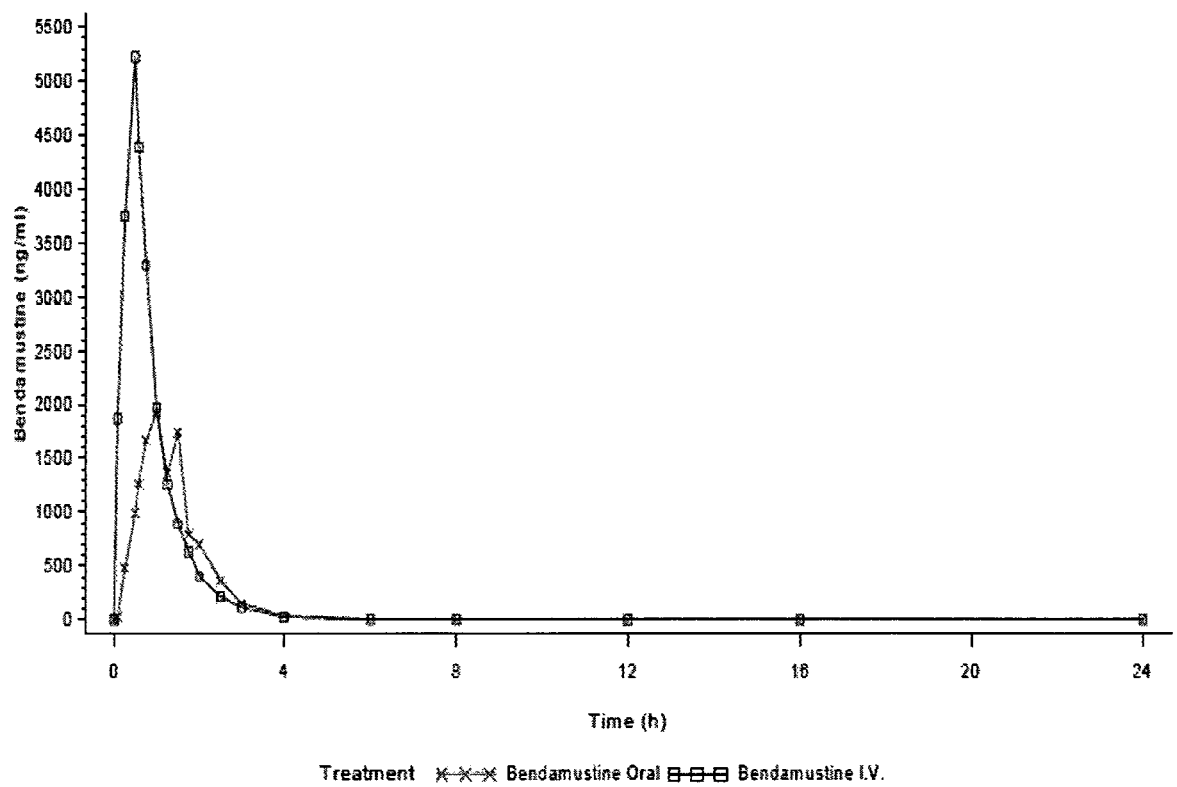
FIG. 2 shows the mean plasma vs. time profile obtained after administering bendamustine hydrochloride in the form of the intravenous preparation, as marketed in Germany under the trademark Ribomustin®, and the liquid filled hard capsule formulation of example 2 to patients with cancer.

The blood concentration-time curve as obtained after evaluating 6 patients is shown in FIG. 2. The mean value for the absolute bioavailability, calculated as $AUC_{oral}$/dose/$AUC_{iv}$/dose*100% was 58.5%, with a standard deviation of 9.3 and an interindividual variation (expressed as % CV) of 15.9.

Therefore the bioavailability of bendamustine hydrochloride from the oral formulation of example 2 was found to be in accordance with that previously reported for bendamustine-containing capsules in the literature (Preiss), but the interpatient variability is much lower.

INDUSTRIAL APPLICABILITY

The compositions according to the present invention show many advantages. They can be easily used by the patient without assistance of supervisory medical staff. Hence the time-consuming trips to the hospital may become obsolete, thereby increasing the patient compliance. Further there is the advantage that hospital staff is less exposed to the contact with the cytotoxic material, thereby decreasing occupational hazards. Also there is less environmental hazard, as no vials containing the cytotoxic compound need to be discarded.

The dosage forms can be swallowed as such, which means that the patient does not need to wait until dissolution of the active ingredient has been achieved. On top of that swallowing the medication is a preferred way of taking it, in order to avoid any contact of the active ingredient with the oral mucosa. Further due to the good stability of the dosage forms they can be easily stored at room temperature and without the need of any special storage conditions.

By using the dosage forms according to the present invention, a considerable reduction of the volume of the dosage form may be achieved. The reduced size is desirable both from a manufacturing and handling standpoint and patient compliance.

Pharmaceutical compositions show a high dissolution in vitro which should reduce the degradation of bendamustine in vivo. Thus the inventive compositions may show an improved bioavailability profile of the bendamustine in vivo, as compared to prior art oral formulations.

The invention claimed is:

1. An oral pharmaceutical composition in a stable dosage form, comprising bendamustine or a pharmaceutically acceptable ester, salt or solvate thereof as an active ingredient, and a pharmaceutically acceptable excipient, which is a pharmaceutically acceptable non-ionic surfactant having a hydrophilic-lipophilic balance (HLB) of between 12 and 18 and a melting point between 5° C. and 37° C., and is selected from the group consisting of a macrogol glycerol hydroxystearate, polyoxyl-35-castor oil, and ethylene oxide/propylene oxide block copolymer, wherein the pharmaceutical composition has a dissolution of the bendamustine of at least 80% in 60 minutes as measured with a paddle apparatus at 50 rpm in 500 ml of a dissolution medium at a pH of 1.5 according to the European Pharmacopoeia.

2. The pharmaceutical composition according to claim 1, wherein the active ingredient is bendamustine hydrochloride.

3. The pharmaceutical composition according to claim 1 wherein the composition comprises 10 to 1000 mg, 25 to 600 mg, 50 to 200 mg or about 100 mg of the active ingredient.

4. The pharmaceutical composition according to claim 1, wherein the composition further comprises colloidal silicon dioxide.

5. The pharmaceutical composition according to claim 1, wherein the composition further comprises lauroyl macrogol glycerides.

6. The pharmaceutical composition according to claim 1, wherein the composition is in a hard gelatine capsule.

7. A method of treating a medical condition selected from the group consisting of chronic lymphocytic leukemia, acute lymphocytic leukemia, chronic myelocytic leukemia, acute myelocytic leukemia, Hodgkin's disease, non-Hodgkin's lymphoma, multiple myeloma, breast cancer, ovarian cancer, small cell lung cancer, non-small cell lung cancer, and an autoimmune disease in a human subject comprising administering the pharmaceutical composition of claim 1 to the human subject.

8. The method according to claim 7, wherein the pharmaceutical composition is administered in combination with at least one further active agent, wherein said further active agent is given prior, concurrently, or subsequently to the administration of the pharmaceutical composition and is selected from the group consisting of an antibody specific for CD20, an anthracyclin derivative, a vinca alkaloid or a platin derivative.

9. The method according to claim 8, wherein the antibody specific for CD20 is rituximab; the anthracyclin derivative is doxorubicin or daunorubicin; the vinca alkaloid is vincristine and the platin derivative is cisplatin or carboplatin.

10. The method according to claim 7, wherein the pharmaceutical composition is administered in combination with at least one corticosteroid, wherein said corticosteroid is given prior, concurrently, or subsequently to the administration of the pharmaceutical composition.

11. The pharmaceutical composition according to claim 10, wherein the corticosteroid is prednisone or prednisolone.

12. The pharmaceutical composition according to claim 1, wherein the pharmaceutically acceptable excipient is macrogol glycerol hydroxystearate.

13. The pharmaceutical composition according to claim 1, wherein the pharmaceutically acceptable excipient is polyoxyl-35-castor oil.

14. The pharmaceutical composition according to claim 1, wherein the pharmaceutically acceptable excipient is ethylene oxide/propylene oxide block copolymer.

15. The pharmaceutical composition according to claim 1, wherein the composition is in a solid dosage form.

16. The pharmaceutical composition according to claim 1, wherein the composition comprises from about 50 mg to about 1000 mg of the bendamustine as a daily dosage amount.

* * * * *